United States Patent
Hong

(10) Patent No.: US 10,342,934 B2
(45) Date of Patent: Jul. 9, 2019

(54) SPRAYER AND SPRAY CONTROL APPARATUS

(71) Applicant: SMBURE CO., LTD., Gwangju (KR)

(72) Inventor: Gi Sool Hong, Gwangju (KR)

(73) Assignee: SMBURE CO., LTD., Gwangju (KR)

( * ) Notice: Subject to any disclaimer, the term of this patent is extended or adjusted under 35 U.S.C. 154(b) by 895 days.

(21) Appl. No.: 14/923,311

(22) Filed: Oct. 26, 2015

(65) Prior Publication Data

US 2016/0303335 A1 Oct. 20, 2016

(30) Foreign Application Priority Data

Apr. 17, 2015 (KR) .................. 10-2015-0054337

(51) Int. Cl.
| | |
|---|---|
| *A61M 11/00* | (2006.01) |
| *A61M 11/02* | (2006.01) |
| *A61M 15/00* | (2006.01) |
| *A61M 16/20* | (2006.01) |
| *A61M 16/00* | (2006.01) |

(52) U.S. Cl.
CPC ........ *A61M 11/02* (2013.01); *A61M 15/0006* (2014.02); *A61M 15/0025* (2014.02); *A61M 16/0066* (2013.01); *A61M 16/20* (2013.01); *A61M 2205/123* (2013.01); *A61M 2206/16* (2013.01); *A61M 2206/18* (2013.01); *A61M 2209/086* (2013.01)

(58) Field of Classification Search
CPC .............. A61M 11/02; A61M 15/0006; A61M 15/0025; A61M 16/20; A61M 16/0066; A61M 2205/123; A61M 2206/16; A61M 2206/18; A61M 2209/086; B05B 1/12; B05B 3/105; B05B 7/0075; B05B 7/045; B05B 7/06
USPC ........ 239/302, 311, 418, 423, 424, 405, 399
See application file for complete search history.

(56) References Cited

U.S. PATENT DOCUMENTS

| | | | | |
|---|---|---|---|---|
| 21,586 | A | * 9/1858 | Wood | B05B 7/0815 239/290 |
| 1,051,672 | A | * 1/1913 | Boudreaux | F23D 14/42 239/290 |
| 1,349,154 | A | * 8/1920 | Holton | B05B 7/0815 239/290 |

(Continued)

FOREIGN PATENT DOCUMENTS

| | | |
|---|---|---|
| KR | 10-1079206 | 11/2011 |
| KR | 10-1153188 | 6/2012 |

(Continued)

*Primary Examiner* — Viet Le

(57) ABSTRACT

Disclosed herein is a sprayer which may include, but is not limited to, a main body with a neck an inner cross section area of which gradually decreases; an air blowing module installed for air in the inside of the main body to be discharged to the outside; a liquid medicine container installed at a lower side of the main body and having air holes at a lid of the liquid medicine container; a nozzle cap having a minimum diameter part at an inner intermediate portion and assembled to the neck of the main body; a nozzle a rear end of which is open and connected to an end of a liquid supply pipe; and a rib which is configured to support in such a way that a central axis of the nozzle can position on a central axis of the nozzle.

16 Claims, 14 Drawing Sheets

(56) References Cited

U.S. PATENT DOCUMENTS

| | | | | |
|---|---|---|---|---|
| 1,430,533 A * | 10/1922 | Brown | B05B 7/12 | 137/607 |
| 1,438,239 A * | 12/1922 | Heinrich | B05B 7/0815 | 239/290 |
| 1,469,479 A * | 10/1923 | Kent | F23D 11/10 | 239/405 |
| 1,586,009 A * | 5/1926 | Shelburne | B05B 7/0815 | 239/133 |
| 1,769,428 A * | 7/1930 | Gatchet | A01C 23/042 | 239/317 |
| 1,822,743 A * | 9/1931 | Mitchell | B05B 7/2437 | 239/348 |
| 1,853,636 A * | 4/1932 | Perrin | B05B 7/0815 | 239/290 |
| 1,881,570 A * | 10/1932 | Hermann | B05B 7/2416 | 138/43 |
| 1,911,366 A * | 5/1933 | Kitto | B05B 7/2432 | 239/290 |
| 1,968,992 A * | 8/1934 | Conkling | B05B 7/162 | 222/146.5 |
| 2,104,761 A * | 1/1938 | Richter | F23D 14/38 | 239/290 |
| 2,138,300 A * | 11/1938 | Gustafsson | B05B 7/0815 | 239/290 |
| 2,198,998 A * | 4/1940 | Honsberger | B01F 3/04007 | 111/7.1 |
| 2,207,655 A * | 7/1940 | Cain | F23D 14/40 | 239/290 |
| 2,214,035 A * | 9/1940 | Tracy | B05B 7/0475 | 239/290 |
| 2,235,278 A * | 3/1941 | Brunner | B05B 7/1418 | 111/7.2 |
| 2,322,296 A * | 6/1943 | Hunter | B60S 3/044 | 239/311 |
| 2,376,413 A * | 5/1945 | Babcock | F23D 14/54 | 239/290 |
| 2,514,748 A * | 7/1950 | Di Stefano | B05B 1/28 | 239/105 |
| 2,561,592 A * | 7/1951 | Palmer | F24F 6/04 | 239/43 |
| 2,705,171 A * | 3/1955 | Ziherl | B05B 7/10 | 239/344 |
| 2,817,000 A * | 12/1957 | Scheid | A45D 20/08 | 34/96 |
| 2,916,873 A * | 12/1959 | Walker | F02K 9/82 | 137/803 |
| 3,152,065 A * | 10/1964 | Sharp | B01J 8/1827 | 196/127 |
| 3,258,578 A * | 6/1966 | Ferris | B08B 3/028 | 134/36 |
| 3,332,231 A * | 7/1967 | Walsh | F02M 19/035 | 239/405 |
| 3,401,850 A * | 9/1968 | Anderson | B65D 25/38 | 220/203.11 |
| 3,526,362 A * | 9/1970 | Jackson | B05B 7/226 | 219/76.14 |
| 3,905,752 A * | 9/1975 | Miller | F23D 11/001 | 239/405 |
| 3,964,689 A * | 6/1976 | Horvath, Jr. | B05B 7/2443 | 239/318 |
| 4,114,022 A * | 9/1978 | Braulke, III | A45D 20/00 | 132/212 |
| 4,185,778 A * | 1/1980 | Drlik | B05B 7/0075 | 239/405 |
| 4,201,538 A * | 5/1980 | Kopp | F23D 11/40 | 431/351 |
| 4,270,576 A * | 6/1981 | Takeda | B01F 5/0451 | 137/888 |
| 4,341,347 A * | 7/1982 | DeVittorio | B05B 5/03 | 239/3 |
| 4,530,469 A * | 7/1985 | Muck | B05B 7/24 | 239/124 |
| 4,555,232 A * | 11/1985 | Raccah | A45D 20/06 | 126/401 |
| 4,573,636 A * | 3/1986 | Dilworth | F25C 3/04 | 239/2.2 |
| 4,579,280 A * | 4/1986 | von Ruhling | B05B 7/205 | 239/400 |
| 4,684,296 A * | 8/1987 | Horii | B65G 53/42 | 137/1 |
| 4,721,246 A * | 1/1988 | Lefebvre | A01M 1/2033 | 108/103 |
| 4,789,104 A * | 12/1988 | Anderson | B05B 1/12 | 239/441 |
| 4,839,106 A * | 6/1989 | Steiner | B01F 3/04007 | 239/289 |
| 4,923,121 A * | 5/1990 | Boyer | B05B 7/149 | 239/427.3 |
| 5,226,567 A * | 7/1993 | Sansalone | A01M 9/0092 | 222/195 |
| 5,327,883 A * | 7/1994 | Williams | A61K 9/0075 | 128/203.12 |
| 5,649,370 A * | 7/1997 | Russo | A45D 20/12 | 34/97 |
| 5,693,267 A * | 12/1997 | Beshore | B01F 3/04021 | 261/142 |
| 6,003,787 A * | 12/1999 | Fisher | A01M 7/0017 | 239/355 |
| 6,015,530 A * | 1/2000 | Porcello | A01N 59/12 | 422/37 |
| 6,092,260 A * | 7/2000 | Kai | B05B 7/2435 | 15/320 |
| 6,141,967 A * | 11/2000 | Angel | F23R 3/14 | 239/405 |
| 6,334,579 B1 * | 1/2002 | Zarbi | B05B 7/0475 | 239/405 |
| 6,817,183 B2 * | 11/2004 | Modi | F23D 11/107 | 239/403 |
| 6,837,447 B1 * | 1/2005 | Clark | A01M 7/0003 | 239/142 |
| 6,883,732 B2 * | 4/2005 | Hasegawa | B05B 3/00 | 239/318 |
| 6,889,773 B2 * | 5/2005 | Hanratty | A62C 5/02 | 169/14 |
| 6,986,217 B2 * | 1/2006 | Leung | D06F 73/00 | 38/77.83 |
| 7,021,391 B2 * | 4/2006 | Schasteen | A62C 15/00 | 169/14 |
| 7,087,115 B1 * | 8/2006 | Moein | B05B 7/0861 | 118/300 |
| 7,168,635 B2 * | 1/2007 | Amaduzzi | B05B 7/12 | 239/318 |
| 7,207,501 B2 * | 4/2007 | Hanratty | A62C 5/02 | 169/14 |
| 7,300,003 B1 * | 11/2007 | Kreikemeier | A01D 43/14 | 239/654 |
| 7,449,068 B2 * | 11/2008 | Lichtblau | C23C 4/12 | 118/302 |
| 7,559,490 B2 * | 7/2009 | Rappin | B05B 7/2435 | 239/154 |
| 7,575,182 B2 * | 8/2009 | Rogers, II | F26B 3/12 | 239/290 |
| 7,644,871 B2 * | 1/2010 | Ramanan | H01L 21/67126 | 228/33 |
| 7,673,813 B2 * | 3/2010 | Raffenberg | A01M 7/0021 | 137/595 |
| 7,676,952 B2 * | 3/2010 | Nakagawa | A45D 20/12 | 239/690 |
| 7,708,208 B1 * | 5/2010 | Scheer | B05B 7/0408 | 239/1 |
| 7,717,358 B2 * | 5/2010 | Noujaim | B05B 7/205 | 239/135 |
| 7,735,748 B1 * | 6/2010 | Scheer | B05B 7/066 | 174/59 |
| 7,863,560 B2 * | 1/2011 | Schaumloffel | B05B 7/066 | 239/290 |
| 7,992,809 B1 * | 8/2011 | Barnett | B05B 7/0416 | 222/190 |

(56) References Cited

U.S. PATENT DOCUMENTS

| | | | | |
|---|---|---|---|---|
| 8,245,630 B2* | 8/2012 | Houraney | A47J 36/2483 | 126/226 |
| 8,286,836 B2* | 10/2012 | Yates | B05B 7/0037 | 222/145.5 |
| 8,353,467 B2* | 1/2013 | Hasegawa | B05B 3/00 | 239/227 |
| 8,444,061 B2* | 5/2013 | Van Den Berg | B05B 7/0466 | 239/105 |
| 8,490,572 B2* | 7/2013 | Mitsui | B05B 5/0426 | 118/300 |
| 8,523,088 B2* | 9/2013 | Mueller | B05B 7/1409 | 239/310 |
| 8,628,029 B2* | 1/2014 | Munn | B05B 7/0815 | 239/290 |
| 8,827,176 B2* | 9/2014 | Browning | F23D 14/52 | 239/13 |
| 8,864,051 B2* | 10/2014 | Lin | B05B 3/0409 | 239/240 |
| 8,967,496 B1* | 3/2015 | Blake | B05B 7/0475 | 239/318 |
| 9,022,073 B2* | 5/2015 | Strauli | E03C 1/046 | 137/888 |
| D751,178 S* | 3/2016 | Gibson | D23/233 | |
| 9,635,922 B2* | 5/2017 | Logsdon | A45D 20/12 | |
| 2001/0003353 A1* | 6/2001 | Kawamoto | A47K 7/04 | 239/310 |
| 2001/0020649 A1* | 9/2001 | Miquel | F04F 5/461 | 239/310 |
| 2002/0030121 A1* | 3/2002 | Kyotani | F04F 5/16 | 239/310 |
| 2002/0185550 A1* | 12/2002 | Ganan-Calvo | A61M 15/0065 | 239/290 |
| 2003/0019952 A1* | 1/2003 | Hunter | B05B 7/062 | 239/290 |
| 2003/0042330 A1* | 3/2003 | Streutker | B05B 9/0861 | 239/337 |
| 2004/0046040 A1* | 3/2004 | Micheli | B05B 1/26 | 239/11 |
| 2005/0108889 A1* | 5/2005 | Leventhal | A45D 20/122 | 34/96 |
| 2005/0269425 A1* | 12/2005 | Gohring | B05B 7/2416 | 239/398 |
| 2005/0279862 A1* | 12/2005 | Mao | F23D 11/107 | 239/403 |
| 2005/0284957 A1* | 12/2005 | Haruch | B05B 7/066 | 239/290 |
| 2006/0290014 A1* | 12/2006 | Swoboda | C02F 1/36 | 261/36.1 |
| 2007/0241208 A1* | 10/2007 | Gohring | B05B 7/2402 | 239/296 |
| 2007/0262170 A1* | 11/2007 | Nolte | B05B 5/001 | 239/291 |
| 2007/0262171 A1* | 11/2007 | Wong | B05B 7/0815 | 239/296 |
| 2008/0116753 A1* | 5/2008 | Carlucci | A45D 20/10 | 310/50 |
| 2008/0229606 A1* | 9/2008 | Hirai | A45D 20/12 | 34/97 |
| 2008/0251607 A1* | 10/2008 | Krayer | B05B 7/0081 | 239/290 |
| 2009/0108475 A1* | 4/2009 | Goldmann | F24F 5/0035 | 261/26 |
| 2009/0151717 A1* | 6/2009 | Bowen | A61M 11/041 | 128/200.23 |
| 2010/0206963 A1* | 8/2010 | Huang | B05B 7/0815 | 239/290 |
| 2010/0252656 A1* | 10/2010 | Gerbron | A45D 33/02 | 239/318 |
| 2010/0282866 A1* | 11/2010 | Gilpatrick | B05B 1/34 | 239/310 |
| 2010/0308134 A1* | 12/2010 | Bunnell | B05B 7/0408 | 239/398 |
| 2010/0320289 A1* | 12/2010 | Kuo | B05B 3/022 | 239/290 |
| 2011/0031636 A1* | 2/2011 | Ediger | F24F 6/12 | 261/78.2 |
| 2012/0318890 A1* | 12/2012 | Hopper | B05B 7/2432 | 239/290 |
| 2013/0099020 A1* | 4/2013 | Voser | B05B 1/06 | 239/13 |
| 2013/0157040 A1* | 6/2013 | Petorak | C23C 4/12 | 428/323 |
| 2013/0341427 A1* | 12/2013 | Ukawa | B08B 7/0092 | 239/290 |
| 2015/0217309 A1* | 8/2015 | Ito | B05B 7/0815 | 239/417.3 |
| 2015/0272879 A1* | 10/2015 | Simonyan | B05B 7/0012 | 424/725 |
| 2016/0001305 A1* | 1/2016 | Doak | B05B 1/08 | 239/8 |
| 2016/0303335 A1* | 10/2016 | Hong | A61M 15/0006 | |

FOREIGN PATENT DOCUMENTS

| | | | | |
|---|---|---|---|---|
| KR | 10-1185064 | | 9/2012 | |
| KR | 101185064 B1 | * | 9/2012 | |
| WO | WO-2015190690 A1 | * | 12/2015 | B05B 7/02 |

* cited by examiner

<Prior Art>

SPRAYER AND SPRAY CONTROL APPARATUS

TECHNICAL FIELD

The present invention relates to a sprayer and a spray control apparatus, and in particular to a sprayer and a spray control apparatus wherein a user can start and stop spraying and adjust the amount of spraying in such a way to rotate a nozzle cap covering a nozzle disposed at a front side of a main body, and the inner configuration of the sprayer can be simplified, and power consumption can be saved.

BACKGROUND ART

A sprayer configured to spray over wide area in such a way to apply pressure to liquid may be categorized into various types based on an operation method, use purpose, size, etc. More specifically, various types of sprayers may be necessary since there are various needs based on particle sizes and types and spraying area wherein the particles are sprayed in fog or granular phases which are selected in consideration of use purpose, for example, household use, agricultural use, industrial use, etc. and the target of spraying.

Meanwhile, in case of a sprayer for disease prevention or sterilization, it is advantageous to uniformly spray a liquid medicine over wider area in terms of a disease prevention effect. To this end, it is preferred to use a sprayer which is able to spray particles with tens or hundreds of μm in size.

As mentioned above, the sprayer which is mainly used for disease prevention, disinfection, etc. in general is called a liquid medicine sprayer, a disease prevention device or a sterilization device. As examples of a prior art technology which is related with a sprayer and a spraying apparatus used for disease prevention or disinfection, there are the Korean patent registration number 10-1153188 (liquid medicine spraying apparatus), the Korean patent registration number 10-1185064 (nozzle for spraying fine liquid medicine), and the Korean patent registration number 10-1079206 (swirl formation port for liquid medicine spraying nozzle).

FIG. 1 is a view for describing the configuration of a liquid medicine spraying apparatus which is an example of the prior art technology. In the above conventional liquid medicine spraying apparatus 1 illustrated in FIG. 1, an air blowing fan 20 installed in the inside of a main body 12 is driven, thus generating air. The generated air will turn into a high pressure state as it passes through a narrow passage 24 formed at a rear end of an air nozzle 22, and most of high pressure air is discharged to the outside through the air nozzle 22, and part of the air is supplied to the upper side in a liquid medicine container 30 through a liquid medicine container pressing pipe 26. The high pressure is supplied through the liquid medicine container pressing pipe 26 toward above the upper surface of the liquid filled in the inside of the liquid medicine container 30, whereupon the pressure in the upper space above the surface of the liquid can increase, and the liquid medicine can be discharged to the outside through a liquid medicine pumping pipe 32 the bottom of which is communicatively connected to the bottom of the liquid medicine container 30, and the liquid medicine which has been discharged from the liquid medicine container 30 can flow to the liquid medicine nozzle 36 through the liquid medicine discharge pipe 34 connected to the liquid medicine pumping pipe 32. Meanwhile, since an air nozzle 22 is formed at the circumference of the liquid medicine nozzle 36 so as to discharge high pressure air which is supplied from the air blowing fan 20, the liquid medicine which is discharged through the liquid medicine nozzle 36 may have influence from the high pressure air which is discharged from the air nozzle 22, thus obtaining spray in a fog state.

In order for the liquid medicine in the inside of the liquid medicine container 30 to be sprayed in such a way through the liquid medicine nozzle 36, the liquid medicine container 10 should separately equip with a pipe connection unit 40 which is installed in a section where the main body 12 and the liquid medicine container 30 are assembled, for the sake of organic connections between the liquid medicine container pressing pipe 26, the liquid medicine pumping pipe 32 and the liquid medicine supply pipe 34. In addition, a liquid medicine adjusting unit 38 configured to adjust the sprayed liquid medicine should be installed at an intermediate portion of the liquid medicine discharge pipe 34, and there should be further provided an assembling unit 50 which is able to allow the main body 12 and the liquid medicine container 30 to keep assembled with a pipe connection member 40 being disposed between the main body 12 and the liquid medicine container 30.

As described above, in the above conventional liquid medicine spraying apparatus, part of the pressure which generated at a rear end of the nozzle may be transferred to the liquid medicine container with the aid of the driving of the air blowing fan, and the liquid medicine in the inside of the liquid medicine container can be pumped up by the high pressure air transferred to the liquid medicine container, and the liquid medicine can be sprayed through the liquid medicine nozzle. For the sake of the above mentioned procedures, a plurality of pipes should be installed in the inside of the main body, and a predetermined apparatus for controlling the liquid medicine should be provided at an intermediate portion of the liquid medicine discharge pipe. For this reason, the whole configuration of the liquid medicine spraying apparatus may become complicated.

PRIOR ART TECHNICAL DOCUMENTS

Patent Documents

Korean patent registration number 10-1153188 (Jun. 18, 2012)
Korean patent registration number 10-1185064 (Sep. 21, 2012)
Korean patent registration number 10-1079206 (Nov. 3, 2011)

DISCLOSURE OF THE INVENTION

Accordingly, it is an object of the present invention to provide a sprayer and a spray control apparatus wherein a user can start and stop spraying and adjust the amount of spraying in such a way to rotate a nozzle cap, and the inner configuration of the sprayer can be simplified, and power consumption can be saved.

It is another object of the present invention to provide a sprayer and a spray control apparatus wherein the maintenance of a sprayer will be efficient in such a way that a main body and a liquid medicine container are assembled integral without using any assembling unit.

To achieve the above objects, there is provided a sprayer, which may include, but is not limited to, a main body wherein an air blowing module assembling part is disposed in an inner space formed as housings are assembled from left and right directions, and a neck is disposed at a front portion of the air blowing module assembling part, the neck having an inner cross section area which gradually decreases; an air blowing module which is installed at the air blowing module assembling part in such a way that air in the inside of the main body can be discharged through the neck to the outside; a liquid medicine container which is installed at a lower side of the main body and wherein air holes are formed at a lid of the liquid medicine container disposed on top wherein air can pass through the air holes, a check valve being installed at an inner side of the lid of the liquid medicine container wherein the air holes are formed; a nozzle cap which is formed in a Venturi tube structure wherein a minimum diameter part is formed at an inner intermediate portion and which is assembled to the neck of the main body; a nozzle which is formed in a pipe shape, a rear end of which is open and connected to an end of a liquid supply pipe connected to the liquid medicine container, wherein a plurality of nozzle holes are formed passing through a front end thereof, the nozzle being installed in such a way that a front end wherein the nozzle holes are formed can position at the minimum diameter part of the nozzle cap; and a rib which is configured to support in such a way that a central axis of the nozzle can position on a central axis of the nozzle cap and is formed in such a way that air can pass through the space between the nozzle and the nozzle cap.

In the sprayer according to the present invention, there is further provided a nozzle head which forms a double pipe together with the nozzle at an outer edge portion of the nozzle in a state where an outer end of the rib is connected, the nozzle head being thread-connected to an inner surface of the nozzle cap.

In the sprayer according to the present invention, a front end of the nozzle is formed in a structure wherein the front end thereof protrudes forward relatively more than the front end of the nozzle head.

In the sprayer according to the present invention, the nozzle, the rib and the nozzle head are formed integral, wherein the rib is formed in a pinwheel shape so as to induce swirl in air which passes through.

In the sprayer according to the present invention, a blocking valve is further installed at an intermediate portion of the liquid medicine supply pipe connected to the inside of the liquid medicine container.

In the sprayer according to the present invention, in a state where the nozzle cap and the nozzle head are assembled into one nozzle module, the nozzle cap and the nozzle head are assembled to a neck of the main body, and the nozzle cap or the nozzle head moves forward and backward by means of the rotational operation of the nozzle cap, the interval between the front end of the nozzle and the minimum diameter part of the nozzle cap can be adjusted.

In the sprayer according to the present invention, a rotation rail is disposed at an inner side of the neck of the main body in order for an engaging tongue formed at a rear end of the nozzle cap to be assembled, and a straight movement rail is disposed in order for a straight movement guide formed at the nozzle head to be assembled.

In the sprayer according to the present invention, an operation space is formed at an inner side of the neck of the main body, wherein the nozzle cap can move forward and backward rotating in the operation space.

In the sprayer according to the present invention, an outer surface in a front portion of the nozzle cap is formed in a slip prevention structure.

In the sprayer according to the present invention, a liquid medicine container engaging protrusion for assembling of the liquid medicine container is formed at an inner side of the housings which are disposed at left and right sides of the main body, and a liquid medicine container engaging groove corresponding to the liquid medicine container engaging protrusion is formed at an outer side of the top of the liquid medicine container.

To achieve the above objects, there is provided a spray control apparatus, wherein a sprayer includes a nozzle, an air blowing module for pressurizing air to pass through near the nozzle, a liquid medicine container configured to store liquid medicine which is supplied to the nozzle, and a main body wherein the liquid medicine container, the nozzle, the air blowing module and the liquid medicine container are assembled, which apparatus may include, but is not limited to, a nozzle cap a front portion of which is formed in a Venturi tube structure, wherein the front portion is divided into a larger diameter portion an inner diameter of which gradually decreases with respect to a minimum diameter part, and a small diameter part the diameter of which is larger than the minimum diameter part, an inner rear portion of the nozzle cap being formed of threads, whereupon the rear end of the nozzle cap is assembled to a neck disposed at a front side of the main body; a nozzle head which includes threads on its outer surface to thread-engage with the nozzle cap and is assembled to an inner side of the neck wherein the inner diameter of the nozzle head is formed larger than the outer diameter of the nozzle; and a rib which is disposed between an inner side of the nozzle head and an outer side of the nozzle, wherein since the nozzle cap or the nozzle head moves forward or backward based on a rotational operation of the nozzle cap, a pressure difference in the Venturi tube structure is transferred to the inside of the nozzle, whereupon the fluid in the liquid medicine container can be supplied to the nozzle.

INDUSTRIAL EFFECTS

The sprayer according to the present invention has advantages in the way that it is possible to start and stop spraying and adjust the amount of spraying in such an easy way to adjust the interval between a minimum diameter part and a nozzle hole formed in the inside of a nozzle cap by rotating a nozzle cap covering a nozzle portion in a state where a user has driven an air blowing fan, and a pipe configuration connected to a liquid medicine container and to a nozzle can be made simple.

In particular, the sprayer according to the present invention is configured in such a way that a liquid medicine container can be assembled together when assembling a housing of a main body, whereupon a predetermined unit for assembling a liquid medicine container to a main body or separating the liquid medicine from the main body is not necessary, thus obtaining advantages in terms of maintenance.

BRIEF DESCRIPTION OF THE DRAWINGS

The present invention will become better understood with reference to the accompanying drawings which are given only by way of illustration and thus are not limitative of the present invention, wherein.

MODES FOR CARRYING OUT THE INVENTION

The configuration and operation of the sprayer according to an exemplary embodiment of the present invention will be described in detail with reference to the accompanying drawings.

Figure 1:
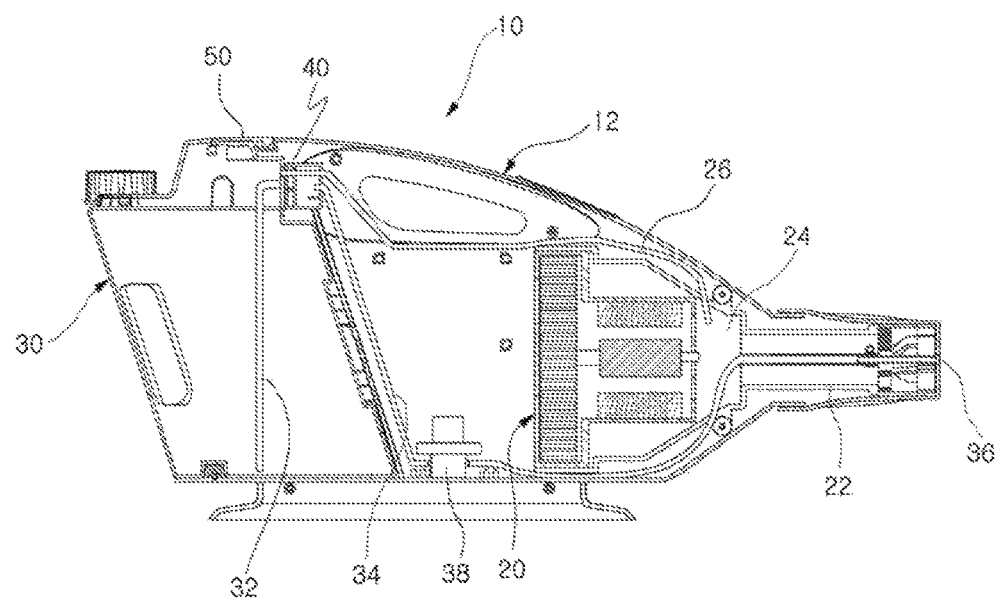
FIG. 1 is a view for describing a configuration of a conventional liquid medicine spraying apparatus.
Figure 2:
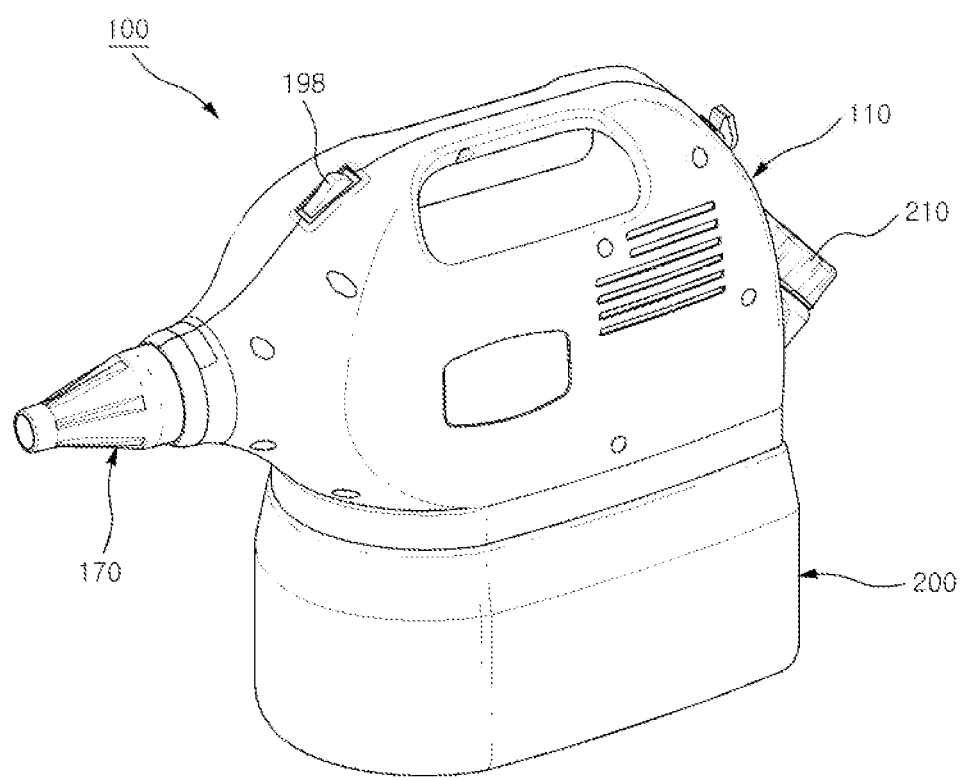
FIG. 2 is a perspective view illustrating a sprayer according to an exemplary embodiment of the present invention.
Figure 3:
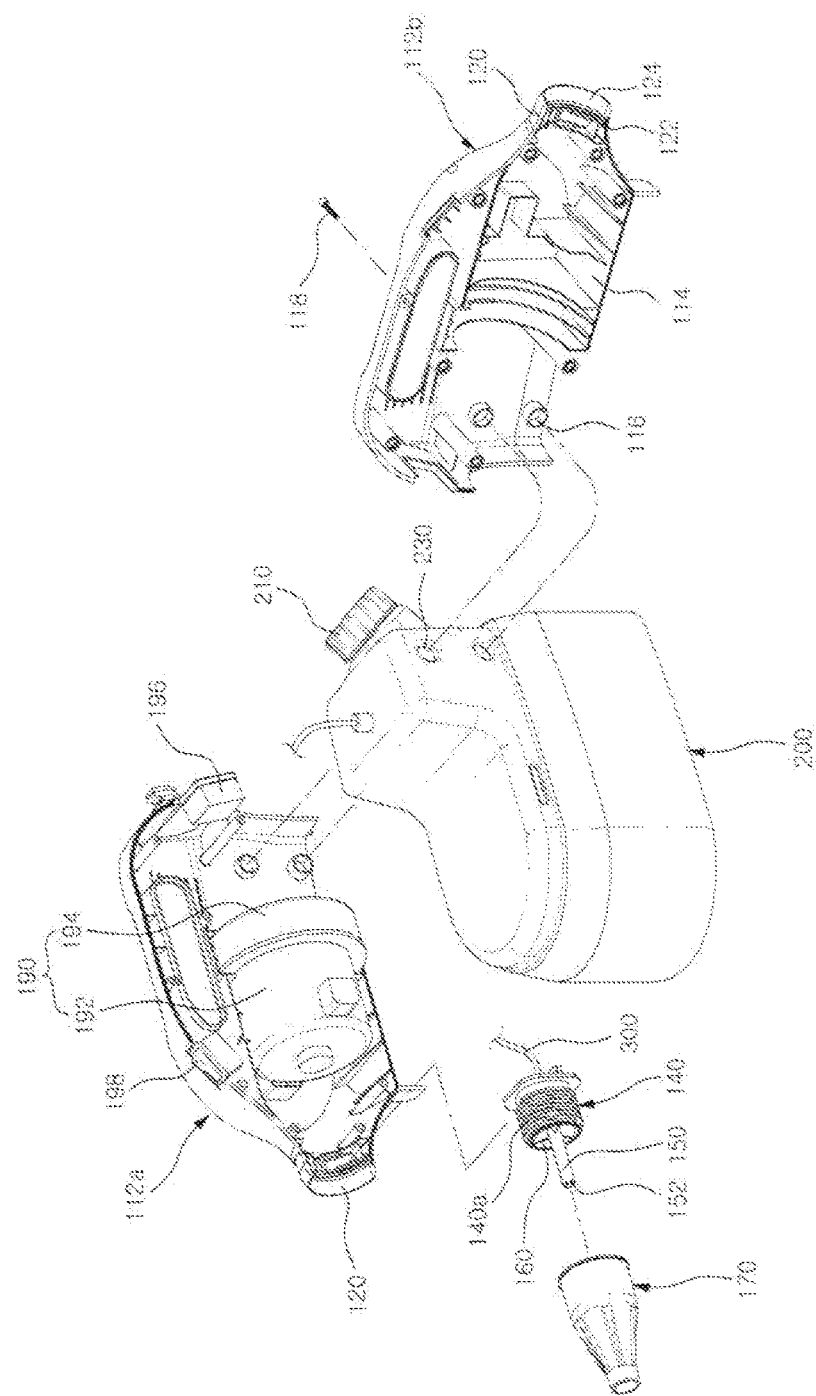
FIG. 3 is a disassembled perspective view illustrating a sprayer according to an exemplary embodiment of the present invention.
Figure 4:
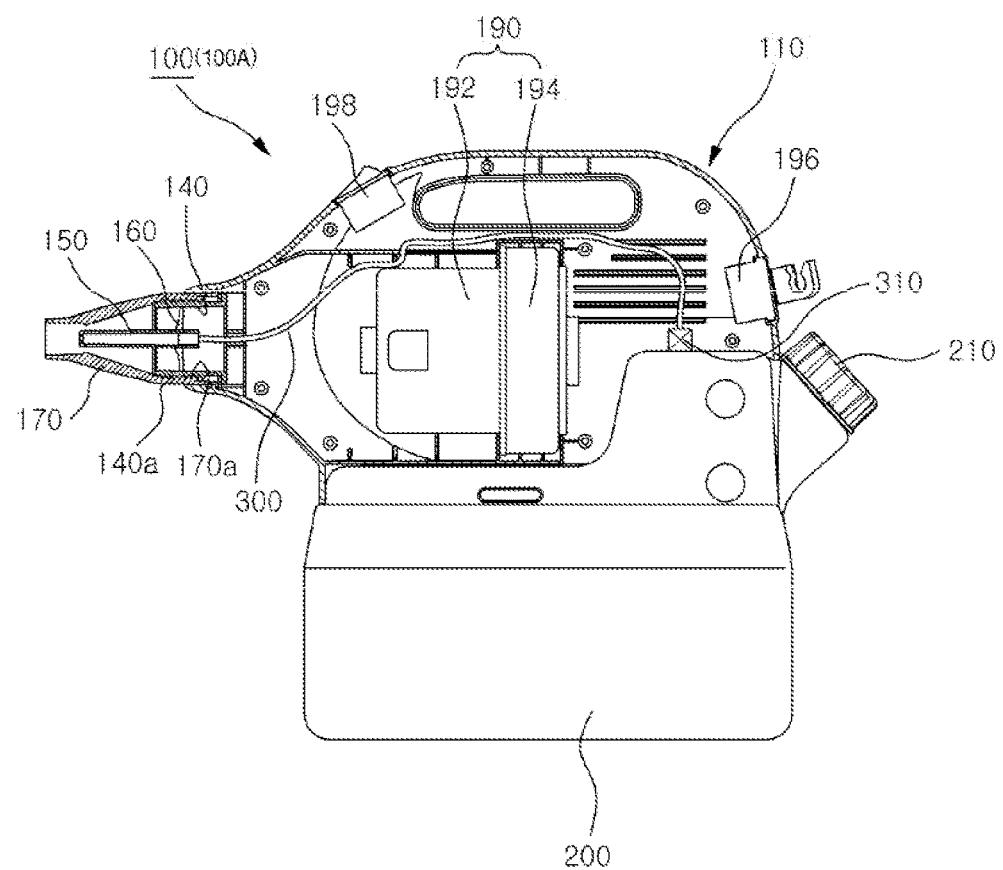
FIG. 4 is a view illustrating an inner configuration of a sprayer according to an exemplary embodiment of the present invention.

FIG. 2 is a perspective view illustrating a sprayer according to an exemplary embodiment of the present invention, FIG. 3 is a disassembled perspective view illustrating a sprayer according to an exemplary embodiment of the present invention, and FIG. 4 is a view illustrating an inner configuration of a sprayer according to an exemplary embodiment of the present invention. Reference number 100 in the drawings represents a sprayer according to an exemplary embodiment of the present invention.

Referring to FIGS. 2 to 4, the main body 110 of the sprayer 100 according to an exemplary embodiment of the present invention may be configured in such a way that a liquid medicine container 200 is assembled integral to the bottom of the main body 110 when assembling the housings 112a and 112b. For this, the housings 112a and 112b are assembled each other from a state where the housings 112a and 112b are separate, and at the bottoms and rear lower sides of the housings 112a and 112b, there is formed an open configuration so as to enable the top of the liquid medicine container 200 to pass.

Meanwhile, a driving motor 192 and an air blowing fan 194 for blowing air when the driving motor 192 is driven is installed in the inside of the main body 110 formed as the housings 112a and 112b are engaged each other from the left and right directions. As seen in the drawings, the driving motor 192 and the air blowing fan 194 may be formed in a form of an air blowing module 190 wherein the driving motor 192 and the air blowing fan 194 are integrated into one body.

An air blowing module assembling part 114 is formed on the inner side surfaces of the housings 112a and 112b in order for the driving motor 192 and the air blowing fan 194 to be installed stable. It is preferred that the air blowing module assembling part 114 may be formed integral with the housings 112a and 112b when forming the housings 112a and 112b. In this way, it is preferred that the housings 112a and 112b are formed in a form of an injection molding product.

The front side of the main body 110 formed as the housings 112a and 112b are engaged each other from the left and right directions is formed in a bottle neck structure wherein the cross section gradually decrease in the forward direction so that air blowing pressure can increase while the air from the air blowing fan 194 is being discharged to the front side of the main body as the air blowing module 190 is driven. The front side of the main body 110 formed in the above bottle neck structure will be called a neck 120. The front side of the main body 110 formed as the housings 112a and 112b are engaged each other has an inner cross section area which gradually decreases. The neck 120 formed at an end portion of the front side may be formed open at its front in a predetermined size.

A nozzle head 140 and a nozzle cap 170 may be installed in the inner side of the neck 120. A nozzle head assembling part 122 and a nozzle cap assembling part 124 may be formed at the inner side of the neck 120 so as to allow the nozzle head 140 and the nozzle cap 170 to be installed without separating from the main body 110.

Figure 5:
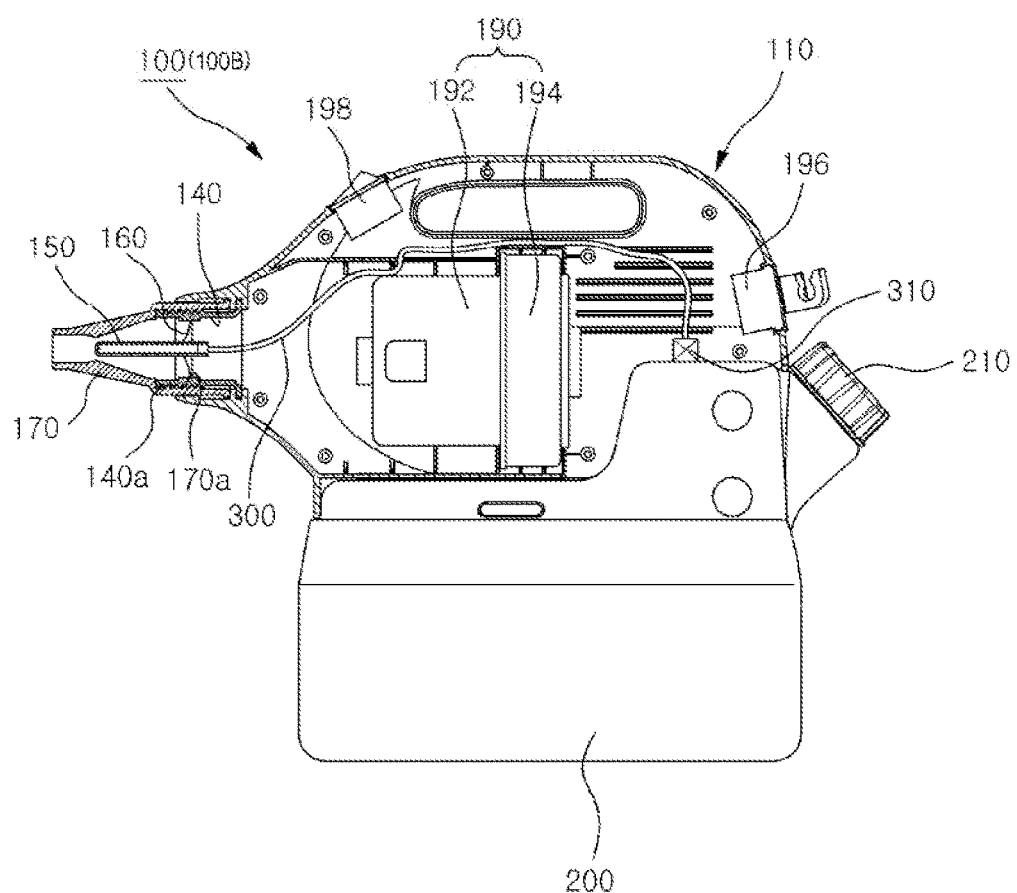
FIG. 5 is a view illustrating an inner configuration of a sprayer according to another exemplary embodiment of the present invention.
Figure 6:
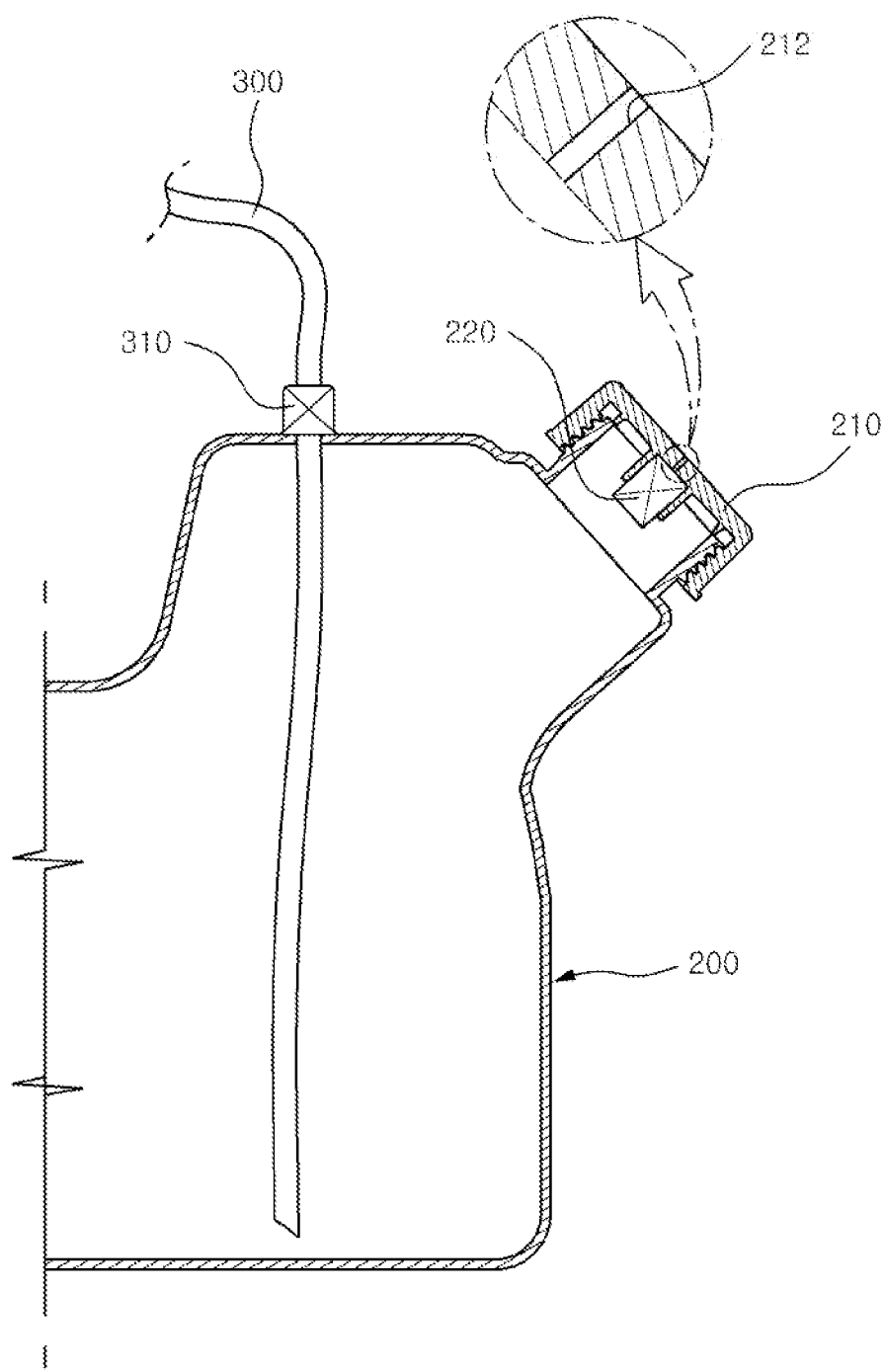
FIG. 6 is a view illustrating the configurations of a liquid medicine and a liquid medicine container stopper which are engaged at a sprayer according to an exemplary embodiment of the present invention.
Figure 7:
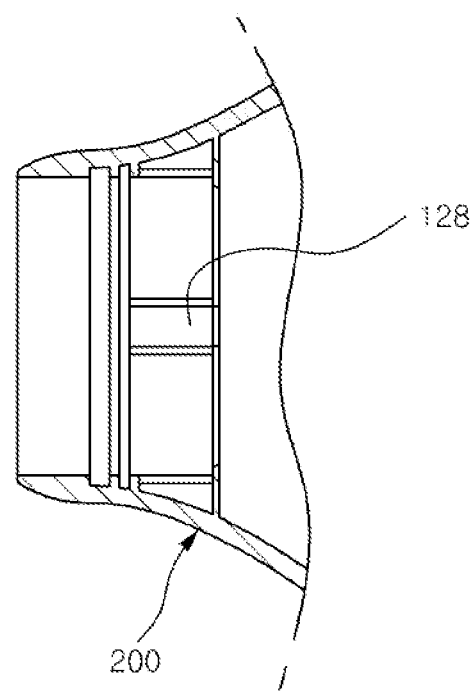
FIGS. 7 to 10 are views for describing in detail the configuration of a sprayer 100a of a nozzle head-movable type according to an exemplary embodiment of the present invention.
Figure 8:
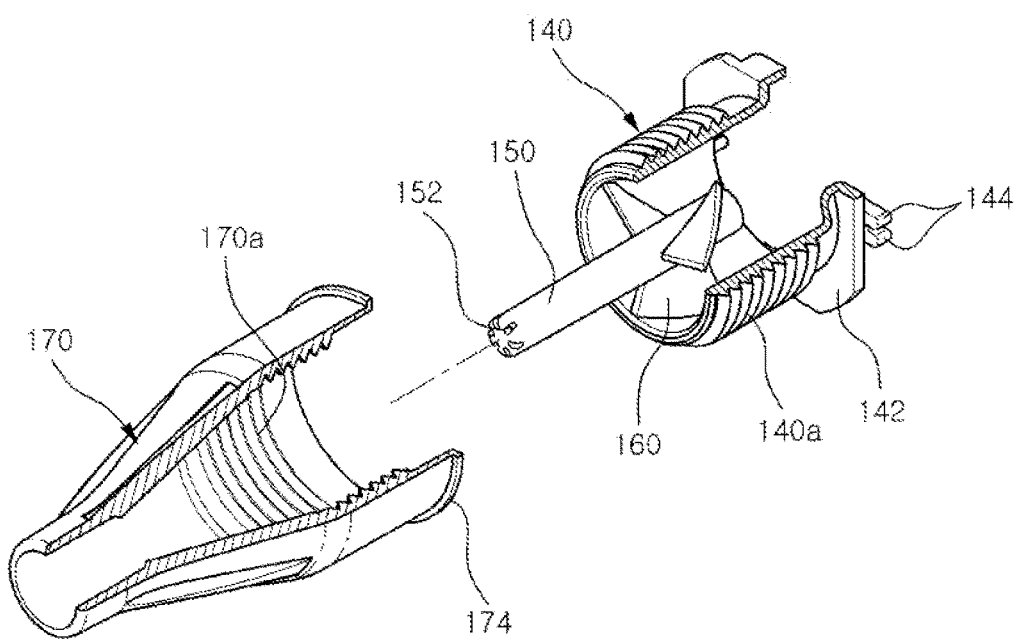
Figure 9:
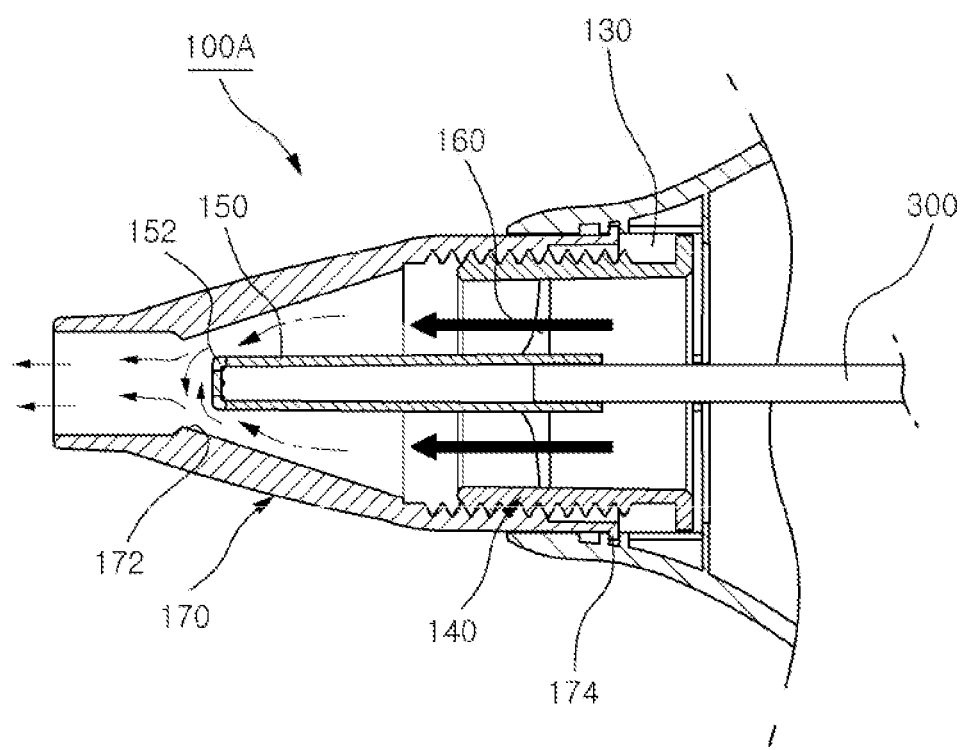
Figure 10:
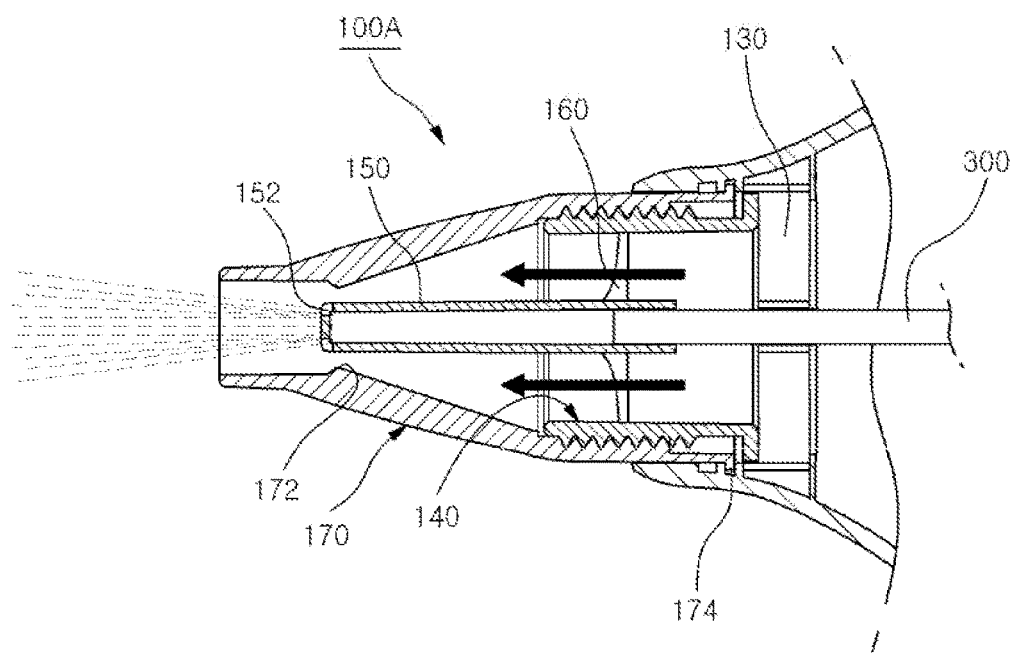
Figure 11:
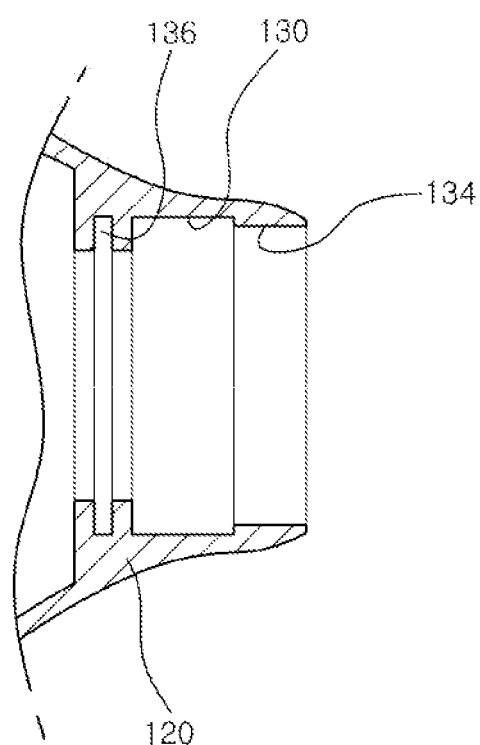
FIGS. 11 to 14 are views for describing in detail the configuration of a sprayer 100b of a nozzle cap-movable type according to another exemplary embodiment of the present invention.
Figure 12:
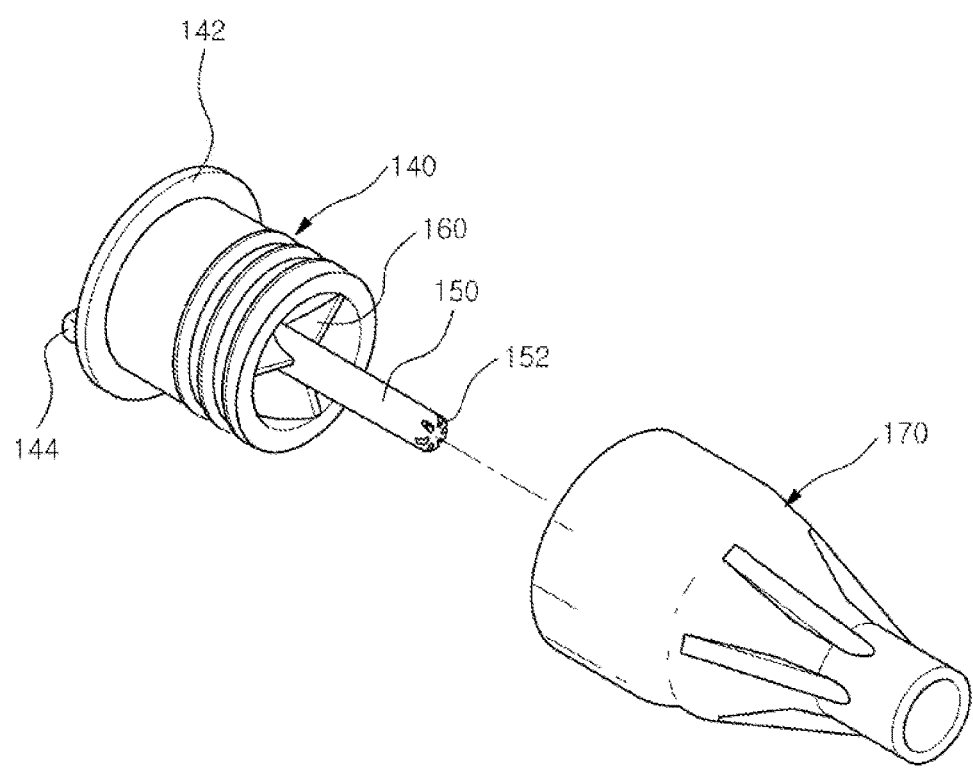
Figure 13:
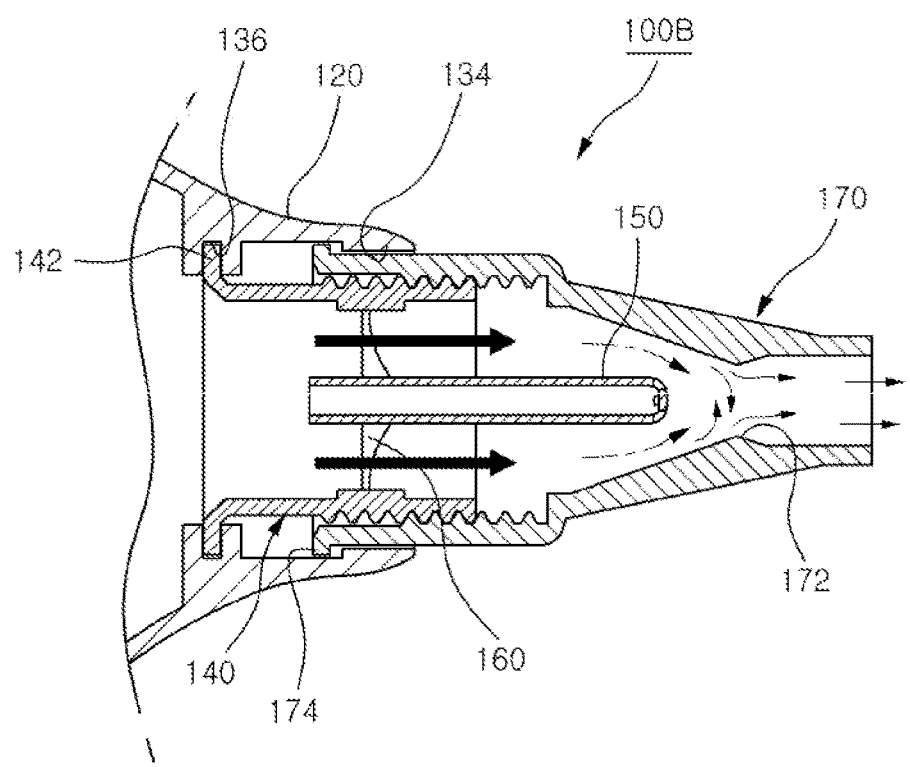
Figure 14:
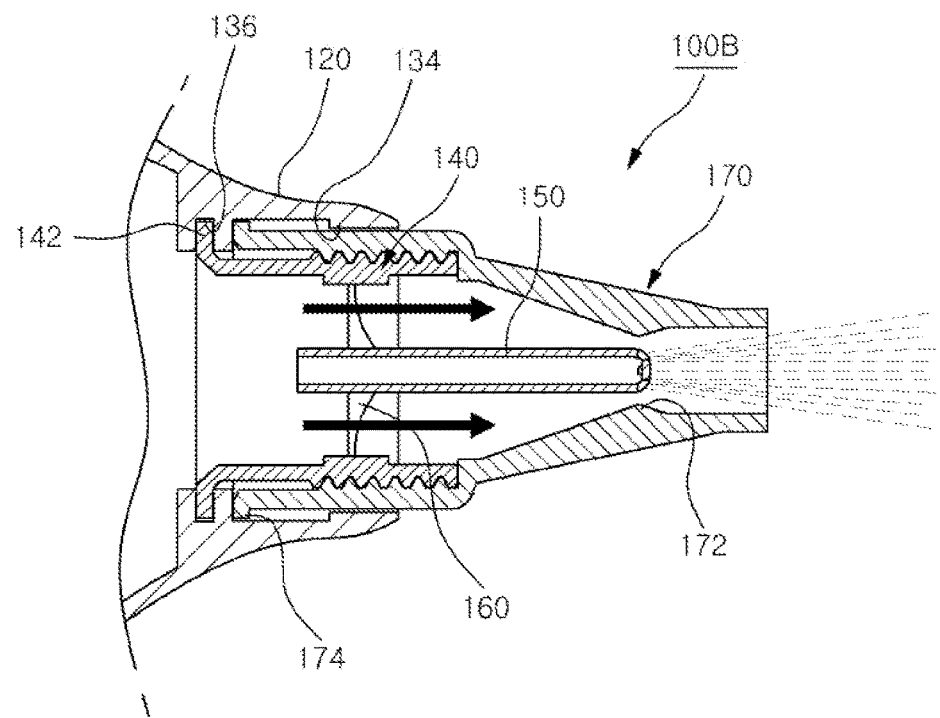

FIGS. 4 and 5 are views for describing the configuration of a sprayer according to another exemplary embodiment of the present invention.

Referring to FIGS. 4 and 5, the nozzle head 140 and the nozzle cap 170 may be configured in such a way that if the nozzle cap 170 rotates by a user's operation, the nozzle head 140 may move forward and backward, and the nozzle cap 170 may rotate in place (hereinafter, it will be called a nozzle head-movable type for better understanding), and if the nozzle cap 170 rotates by a user's operation, the nozzle head 140 may be fixed, and the nozzle cap 170 may move forward and backward (hereinafter, it will be called a nozzle cap-movable type for better understanding).

The basic configurations and operation principles of the sprayer 100a to which the nozzle head-movable type has applied as in FIG. 4 and the sprayer 100b to which the nozzle cap-movable type has applied as in FIG. 5 are same, whereupon only the nozzle head type will be described with respect to the same configurations and operations.

Referring to FIGS. 4 and 5, the nozzle head of the sprayer 100 according to an exemplary embodiment of the present invention may be configured in such a way that a cylinder with a smaller diameter is integrally connected to the inside of a cylinder with a larger diameter by a rib 160. For the sake of easier description, the portion with a larger diameter while forming an outer main body will be called a nozzle head 140, and the portion with a smaller diameter and in the inside of the nozzle head 140 will be called a nozzle 150. In the drawings, the above nozzle 150 has been described as it is formed integral with the nozzle head 140, but the nozzle head 140 and the nozzle 150 may be manufactured separate and then may be integrally assembled later.

A thread 140a may be formed on an outer circumference of the front side of the nozzle head 140, and an engaging tongue 142 may be formed at an end portion of the backside of the nozzle head 140 so as to limit any movement with respect to the nozzle head assembling part 122.

In addition, the front end of the nozzle 150 may project longer than the front end of the nozzle head 140, and the rear end thereof may be formed at a more inner side as compared to the rear end of the nozzle head 140. In particular, a plurality of small sized nozzle holes 152 as illustrated in the drawing are formed passing through the front end of the nozzle 150. It is preferred that the diameter of the nozzle hole 152 is about 1 mm.

The nozzle head 140 and the nozzle 150 may include a rib 160 which is able to connect the inner side of the nozzle head 140 and the outer side of the nozzle 150 so that they can be maintained integral. It is preferred that the rib 160, as illustrated in the drawing, is arranged in a pinwheel shape. If the rib 160 is formed in a pinwheel shape, which is able to allow the nozzle head 140 and the nozzle 150 to be maintained integral, the air flowing between the inner side of the nozzle head 140 and the outer side of the nozzle 150 may easily have a swirl flow, which is advantageous.

It is preferred that the nozzle head 140 is assembled together when the nozzle cap 170 assembled to the neck 120 of the main body 110 is assembled to the main body 110.

As illustrated in the drawings, the outer side of the nozzle cap 170 is assembled to the neck 120 of the main body 110, and the inner side thereof is formed in a cylindrical shape wherein a thread 170a is formed on an inner circumference in a predetermined portion which is thread-engaged to the nozzle head 140, and the remaining portions may be formed in such a way that the inner cross section gradually decreases in the forward direction. In particular, as illustrated in the drawing, when the front end of the nozzle 50 is accommodated to the maximum in the inside of the nozzle cap 170 due to the relative movement of the nozzle head 140 or the nozzle cap 170, the inner cross section area of the nozzle cap 170 may be minimized at the point where the end of the nozzle 150 positions. Namely, a ring shape minimum diameter part 172 may be formed in the inside of the nozzle cap 170 which is configured in such a way that the inner cross section gradually decreases in the forward direction, whereby the inner cross section can be minimized at a point where the end of the nozzle 150 positions. Meanwhile, the front portion of the minimum diameter part 172 may have a larger diameter than the minimum diameter part 172, but may have a smaller diameter than the rear portion of the minimum diameter part 172, which consequently may form a cylindrical shape.

In addition, the front side of the nozzle cap 170 may be formed in a Venturi tube structure wherein a large diameter part and a small diameter part are formed in the front and rear sides with respect to the minimum diameter part 172, whereupon high pressure air which passes through the large diameter part may flow slowly after it has flown at a high speed through the minimum diameter part 172, wherein pressure increases more.

The reason why the minimum diameter part 172 is formed in the inside of the nozzle cap 170 corresponding to the end of the nozzle 150 formed in the inside of the nozzle head 140 is that it needs to provide any condition wherein a more strong swirl can be generated while the swirl formed when a high pressure air passes through the rib 160 formed between the nozzle cap 170 and the nozzle 150 passes through a narrow space. In addition, the swirl formed as it passes through the pinwheel shape rib 160 increases more while it passes through the Venturi tube, and the difference in the pressure between the front side and the rear side with respect to the minimum diameter part 172 increases more, so such a difference in the pressure can apply to the nozzle 150 an end of which positions in the inside of the nozzle cap 70.

In particular, the nozzle cap 170 and the nozzle head 140 are arranged in such a way that their relative positions can be adjusted, whereupon the position of the end of the nozzle 140 can be adjusted with respect to the minimum diameter part 172. More specifically, the size of the cross section area that the air passes through can change depending on a change in the interval of the nozzle 150 with respect to the minimum diameter part 172. For this reason, the difference in the pressure between the front portion and the rear portion of the minimum diameter part can change, which may consequently have effect on the operation of the suction pressure in the inside of the nozzle 150.

Meanwhile, a liquid medicine supply pipe 300 connected with the liquid medicine container 200 may be disposed at a rear end of the nozzle 150. The liquid medicine supply pipe 300 may be configured in a pipe type, but it is advantageous to configure the same in a hose type in terms of the setting of the layout of the inside of the main body 110.

In addition, a blocking valve 310 formed of a solenoid valve may be installed at an intermediate portion of the liquid medicine supply pipe 300 an end of which is accommodated in the inside of the liquid medicine container 200. The blocking valve 310 may be configured to operate in relation with the power switch 198 which may control the on/off operations of the driving motor 192 of the air blowing module 190. To this end, when the user of the sprayer 100 according to an exemplary embodiment of the present invention switches on the power switch 198 so as to use the sprayer, the blocking valve 310 is open as the driving motor 192 is driven, so the liquid medicine can flow through the liquid medicine supply pipe 300. On the contrary, when the user switches off the power switch 198 of the sprayer 100, the operation of the driving motor 192 will stop, and the blocking valve 310 is closed, so the flow of the liquid medicine through the liquid medicine supply pipe 300 can be blocked.

In a state where the air blowing fan 194 is driven, suction force can apply to the nozzle 150 with the aid of change in the pressure which occurs by the interoperation between the nozzle cap 170 and the nozzle head 140, whereupon the liquid contained in the inside of the liquid medicine container 200 can flow through the nozzle 150 toward where the Venturi pipe is formed. In addition, since the high pressure air blown by the air blowing fan 194 is being discharged together with swirl to the outside of the nozzle cap 170, the liquid medicine discharged to the nozzle hole 152 of the nozzle 150 is mixed with the air which discharges through the nozzle cap 170, thus spraying in a fog state.

While the above-described operations are being performed, a certain change in pressure may occur in the inside of the liquid medicine container 200 when the liquid in the inside of the liquid medicine container 200 is discharged through the nozzle 150. In order to compensate such changes in the pressure in the inside of the liquid medicine container 200, it needs to install a check valve 220 at the liquid medicine container stopper 210, the check valve 220 being able to permit external air to flow into the inside of the liquid medicine container 200 while not permitting the liquid in the inside of the liquid medicine container 200 to discharge to the outside.

FIG. 6 is a view illustrating the configuration of a liquid medicine container 200 and a liquid medicine container stopper 210 which are engaged at the sprayer 100 according to an exemplary embodiment of the present invention.

As illustrated in FIG. 6, small size air holes 212 are formed at the liquid medicine container stopper 210, and the check valve 220 is installed at an inner side of the liquid medicine container stopper 210 wherein the air holes 212 are formed. To this end, when the sprayer 100 according to the exemplary embodiment of the present invention operates, the check valve 220 may be operated while the liquid medicine in the inside of the liquid medicine container 200 discharges through the nozzle 150 with the aid of difference in pressure which generates in the Venturi tube based on the interoperation between the nozzle head 140 and the nozzle cap 170, and then the external air of the liquid medicine container 200 may flow into the inside of the liquid medicine container 200, thus performing an efficient spraying.

Meanwhile, when the housings 112a and 112b are engaged each other from the left and right directions, it is preferred that the liquid medicine container 200 is configured in such a way to maintain a state where the liquid medicine container 200 has been engaged to the main body 110 by the liquid medicine container engaging protrusion 116 which is formed at the inner surfaces of the left and right housings 112a and 112b. For this, as illustrated in FIG. 3, a liquid medicine container engaging groove 230 may be formed at the position of the liquid medicine container 200 corresponding to the liquid medicine container engaging protrusion 116. When assembling the sprayer 100 according to the exemplary embodiment of the present invention, in a state where the top of the liquid medicine container 200 may position at the inner sides of the housings 112a and 112b, the liquid medicine container engaging protrusion 116 and the liquid medicine container engaging groove 230 are engaged each other, and then the left and right housings 112a and 112b are engaged each other. To this end, the top of the liquid medicine container 200 may be accommodated in the inside of the main body 110, and the liquid medicine container engaging protrusion 116 and the liquid medicine container engaging groove 230 are engaged each other, so the liquid medicine container 200 can keep consequently being assembled to the main body 110 without using any engaging means. In this way, with the main body 110 and the liquid medicine container 200 being engaged each other, the left and right housings 112a and 112b are engaged each other using an engaging screw 118.

In the drawings which show a configuration of the sprayer according exemplary embodiments of the present invention, reference number 196 represents a power connector to supply electric power to the driving motor 192, and reference number 198 represents a power switch for controlling the on/off of the driving motor 192.

FIGS. 7 to 10 are views for describing in detail the configuration of a sprayer 100a of a nozzle head-movable type according to an exemplary embodiment of the present invention.

As illustrated in FIGS. 7 to 10, in the nozzle head-movable type sprayer 100a, an engaging tongue 174 is formed at a rear end of the nozzle cap 170 so that when the user rotates the nozzle cap 170 assembled to the main body 110, the nozzle cap 170 can rotate in place in the direction where the user rotates, and a ring shaped rotation rail 126 is formed at the nozzle head assembling part 122 at the inner side of the neck 120 corresponding to the engaging tongue 174.

A straight movement rail 128 may be formed at the nozzle head assembling part 122 at the inner side of the neck 120 in order for the nozzle head 140 thread-engaged to the nozzle cap 170 to perform a straight movement in the forward and backward directions within a predetermined stroke range when the nozzle cap 170 rotates. A straight movement guide 144 is formed at the nozzle head 140 for the sake of assembling to the straight movement rail 128.

In addition, an operation portion 130 is formed at an inner side of the neck 120 of the main body 110 in order for the nozzle head 140 to move straightly within a predetermined stroke range when the nozzle cap 170 rotates, and a rear stopper 132 may provided to hook the engaging tongue 142 formed at the nozzle head 140 so as to prevent a predetermined operation from being performed out of a predetermined range in a backward direction.

FIGS. 11 to 14 are views for describing in detail the configuration of a sprayer 100b of a nozzle cap-movable type according to another exemplary embodiment of the present invention.

As illustrated in FIGS. 11 to 14, in the nozzle cap-movable type sprayer 100b, when the user rotates the nozzle cap 170 installed at a front side of the main body 110, the nozzle cap 170 rotates, and the nozzle head 140 thread-engaged to the nozzle cap 170 cannot move straightly in the forward and backward directions, whereby the nozzle cap 170 can move forward and backward. For this, a ring shaped rotation rail 136 is formed at an inner side of the neck 120 corresponding to the engaging tongue 142 formed at a rear end of the nozzle head 140, and the front stopper 34 may protrude inwardly from an inner end portion of the neck 120 of the main body 110, wherein the front stopper 134 is able to hook the engaging tongue 174 formed at a rear end of the nozzle cap 170 in order to prevent any separation of the nozzle cap 170 in the forward direction of the main body 110. At this time, the nozzle head 140 may be fixed at an inner side of the neck 120 of the main body 110.

An operation space may be formed at an inner side of the neck 120 of the main body 110 so that the nozzle cap 170 can move in the forward and backward directions while rotating within a predetermined stroke range.

Therefore, when the user rotates the nozzle cap 170 in the middle of the use of the sprayer 100, the nozzle cap 170 thread-engaged to the fixed nozzle head 140 may rotate in the direction where the user has rotated and may move in the forward and backward directions within a predetermined stroke range, whereupon the interval between the minimum diameter part 172 formed in the inside of the nozzle cap 170 and the nozzle 150 can be adjusted.

As described above, a relative position of the nozzle cap 170 or the nozzle head 140 may change based on the direction where the user rotates the nozzle cap 170 installed at a front side of the sprayer 100, and the interval between the position of the end portion of the nozzle 150 and the position of the minimum diameter part 172 formed at the inner side of the nozzle cap 170 can be adjusted, whereupon a predetermined difference in the pressure can occur near the Venturi pipe wherein the minimum diameter part 172 is formed, and the thusly generated pressure difference may have effect on the inside of the nozzle 150, whereby the liquid medicine filled in the inside of the liquid medicine container 200 can be discharged with the aid of suction force which applies to the nozzle 150.

Meanwhile, the pressure of the suction force which transfers to the nozzle 150 can be adjusted based on the direction where the user rotates the nozzle cap 170 and the degree of rotation, the amount of the liquid medicine discharged through the nozzle 150 can be adjusted. For this reason, there is not a need to separately provide any liquid medicine adjusting means for adjusting the amount of discharge of the liquid medicine. The nozzle cap 170 may allow to start or stop spraying liquid medicine as well as to adjust the amount of liquid medicine.

In case of the nozzle head-movable type sprayer 100a wherein when the nozzle cap 170 is rotated, the nozzle cap 170 rotates in place, and the nozzle head 140 moves forward and backward, there is not any need to change the whole length of the sprayer 100 including the nozzle cap 170, entailing many advantages when packing products.

As the present invention may be embodied in several forms without departing from the spirit or essential characteristics thereof, it should also be understood that the above-described examples are not limited by any of the details of the foregoing description, unless otherwise specified, but rather should be construed broadly within its spirit and scope as defined in the appended claims, and therefore all changes and modifications that fall within the meets and bounds of the claims, or equivalences of such meets and bounds are therefore intended to be embraced by the appended claims.

[Legend of reference numbers]

| | |
|---|---|
| 100, 100a, 100b: Sprayer | |
| 110: Main body | 112a, 112b: Housing |
| 114: Air blowing module assembling part | |
| 116: Liquid medicine engaging protrusion | |
| 120: Neck | 122: Nozzle head assembling part |
| 124: Nozzle cap assembling part | 126: Rotation rail |
| 128: straight movement rail | 130: Operation portion |
| 132: Rear stopper | 140: Nozzle head |
| 150: Nozzle | 152: Nozzle hole |
| 160: Rib | 170: Nozzle cap |
| 172: Minimum diameter part | 174: Engaging tongue |
| 190: Air blowing module | 192: Driving motor |
| 194: Air blowing fan | 200: Liquid medicine container |
| 210: Liquid medicine container stopper | |
| 212: Air hole | |
| 220: Check valve | 230: Liquid medicine engaging groove |
| 300: Liquid medicine supply pipe | 310: Blocking valve |

What is claimed is:

1. A sprayer, comprising:
a main body wherein an air blowing module assembling part is disposed in an inner space, the inner space being formed when housings are assembled, and a neck is disposed at a front portion of the air blowing module assembling part, the neck having an inner cross section area which gradually decreases;
an air blowing module which is installed at the air blowing module assembling part to discharge air in the main body through the neck;
a liquid medicine container which is installed at a lower side of the main body, wherein air holes are formed at a lid of the liquid medicine container, the lid being disposed on a top portion of the liquid medicine container, a check valve being installed at an inner side of the lid of the liquid medicine container;
a nozzle cap which is formed in a Venturi tube structure, the nozzle cap including a minimum diameter part that is formed at an inner intermediate portion and being assembled to the neck of the main body;
a nozzle which is formed in a pipe shape, a rear end of which is open and is connected to an end of a liquid medicine supply pipe, the liquid medicine supply pipe being connected to the liquid medicine container, wherein a plurality of nozzle holes are formed at a front end of the nozzle and penetrate respective portions of the front end, the nozzle being installed to locate the front end of the nozzle proximate to the minimum diameter part of the nozzle cap;
a rib which is configured to locate a central axis of the nozzle to correspond to a central axis of the nozzle cap by supporting the nozzle, air passing through a space between the nozzle and the nozzle cap; and
a nozzle head coupled to the nozzle via the rib such that the nozzle head and the nozzle move together as a single unit.

2. The sprayer of claim 1, wherein the nozzle head is threadly coupled to an inner surface of the nozzle cap.

3. The sprayer of claim 2, wherein the front end of the nozzle protrudes forward in relation to a front end of the nozzle head.

4. The sprayer of claim 3, wherein the rib is formed in a pinwheel shape so as to induce swirl in air which passes through the rib.

5. The sprayer of claim 2, wherein a blocking valve is further installed at an intermediate portion of the liquid medicine supply pipe that is connected to inside of the liquid medicine container.

6. The sprayer of claim 5, wherein the blocking valve is configured to operate in cooperation with a power switch which controls on/off operations of a driving motor of the air blowing module.

7. The sprayer of claim 5, wherein, when the nozzle cap and the nozzle head are assembled into a single nozzle module, the nozzle cap and the nozzle head are assembled to the neck of the main body, and the nozzle cap or the nozzle head moves in a straight line by means of a rotational operation of the nozzle cap to adjust a distance between the front end of the nozzle and the minimum diameter part of the nozzle cap.

8. The sprayer of claim 5, wherein a rotation rail is disposed at an inner side of the neck of the main body and configured to be coupled to an engaging tongue that is formed at a rear end of the nozzle cap, and a straight movement rail is disposed at the inner side of the neck of the main body and is assembled to a straight movement guide that is formed at the nozzle head.

9. The sprayer of claim 5, wherein an operation space is formed at an inner side of the neck of the main body, the nozzle cap moving in a straight line in the operation space when the nozzle cap rotates.

10. The sprayer of claim 5, wherein an outer surface in a front portion of the nozzle cap is formed in a slip prevention structure.

11. The sprayer of claim 5, wherein a liquid medicine container engaging protrusion is disposed at an inner side of each of the housings, and a liquid medicine container engaging groove corresponding to the liquid medicine container engaging protrusion is disposed at an outer side of the liquid medicine container.

12. A spray control apparatus, wherein a sprayer includes a nozzle, an air blowing module, a liquid medicine container configured to store liquid medicine which is supplied to the nozzle, and a main body in which the liquid medicine container, the nozzle, the air blowing module, and the liquid medicine container are assembled, the apparatus comprising:
a nozzle cap having a front portion that is formed in a Venturi tube structure, wherein the front portion is divided into a larger diameter part and a small diameter part with respect to a minimum diameter part, the small diameter part having a diameter that is larger than a diameter of the minimum diameter part, an inner rear portion of the nozzle cap being formed of threads to assemble a rear end of the nozzle cap to a neck that is disposed at a front side of the main body;
a nozzle head which includes threads on its outer surface that are threadly coupled with the nozzle cap and is assembled to an inner side of the neck, an inner diameter of the nozzle head being larger than an outer diameter of the nozzle; and
a rib which is disposed between an inner side of the nozzle head and an outer side of the nozzle, the nozzle head and the nozzle being coupled via the rib such that the nozzle head and the nozzle move together as a single unit, wherein the nozzle cap or the nozzle head moves in a straight line in response to a rotational operation of the nozzle cap, and a pressure difference in the Venturi tube structure is transferred to inside of the nozzle to supply fluid in the liquid medicine container to the nozzle.

13. The apparatus of claim 12, wherein the rib, the nozzle head, and the rib are integrally formed.

14. The apparatus of claim 12, wherein the rib is formed in a pinwheel shape and includes a plurality of blades that are arranged at regular intervals.

15. A sprayer comprising:
a main body wherein an air blowing module assembling part is disposed in an inner space, the inner space being formed when housings are assembled, and a neck is disposed at a front portion of the air blowing module assembling part, the neck having an inner cross section area which gradually decreases;
an air blowing module which is installed at the air blowing module assembling part to discharge air in the main body through the neck;
a liquid medicine container which is installed at a lower side of the main body, wherein air holes are formed at a lid of the liquid medicine container, the lid being disposed on a top portion of the liquid medicine container, a check valve being installed at an inner side of the lid of the liquid medicine container;
a nozzle cap which is formed in a Venturi tube structure, the nozzle cap including a minimum diameter part that is formed at an inner intermediate portion and assembled to the neck of the main body;
a nozzle which is formed in a pipe shape, a rear end of which is open and is connected to an end of a liquid supply pipe, the liquid supply pipe being connected to the liquid medicine container, wherein a plurality of nozzle holes are formed at a front end of the nozzle and penetrate respective portions of the front end, the nozzle being installed to locate the front end of the nozzle proximate to the minimum diameter part of the nozzle cap;
a rib which is configured to locate a central axis of the nozzle to correspond to a central axis of the nozzle cap by supporting the nozzle and configured to pass air through a space between the nozzle and the nozzle cap; and
a nozzle head coupled to the nozzle,
wherein either one of the nozzle cap and the nozzle head moves in a straight line by means of a rotational operation of the nozzle cap to adjust a distance between the front end of the nozzle and the minimum diameter part of the nozzle cap.

16. The sprayer of claim 15, wherein the nozzle head and the nozzle are coupled via the rib such that the nozzle head and the nozzle move together as a single unit.

* * * * *